(12) United States Patent
Jeannin (10) Patent No.: US 10,898,467 B2
(45) Date of Patent: Jan. 26, 2021

(54) VETERINARY FORMULATIONS

(71) Applicant: BOEHRINGER INGELHEIM ANIMAL HEALTH USA INC., Duluth, GA (US)

(72) Inventor: Philippe Jeannin, Sainte Foy les Lyon (FR)

(*) Notice: Subject to any disclaimer, the term of this patent is extended or adjusted under 35 U.S.C. 154(b) by 0 days.

(21) Appl. No.: 15/777,886

(22) PCT Filed: Nov. 16, 2016

(86) PCT No.: PCT/US2016/062364
§ 371 (c)(1),
(2) Date: May 21, 2018

(87) PCT Pub. No.: WO2017/091417
PCT Pub. Date: Jun. 1, 2017

(65) Prior Publication Data
US 2018/0344697 A1    Dec. 6, 2018

(30) Foreign Application Priority Data

Nov. 24, 2015  (GB) .................................. 1520724.4

(51) Int. Cl.
| | | |
|---|---|---|
| *A61K 31/415* | (2006.01) | |
| *A01N 47/02* | (2006.01) | |
| *A01N 43/40* | (2006.01) | |
| *A01N 49/00* | (2006.01) | |
| *A01N 25/02* | (2006.01) | |
| *A01N 25/30* | (2006.01) | |
| *A01N 25/04* | (2006.01) | |
| *A61K 47/26* | (2006.01) | |
| *A61K 45/06* | (2006.01) | |
| *A61K 31/4015* | (2006.01) | |
| *A61K 47/32* | (2006.01) | |
| *A61P 33/14* | (2006.01) | |
| *A61K 9/00* | (2006.01) | |
| *A61K 31/231* | (2006.01) | |
| *A61K 31/4402* | (2006.01) | |
| *A61K 47/10* | (2017.01) | |
| *A61K 47/22* | (2006.01) | |

(52) U.S. Cl.
CPC ............ *A61K 31/415* (2013.01); *A01N 25/02* (2013.01); *A01N 25/04* (2013.01); *A01N 25/30* (2013.01); *A01N 43/40* (2013.01); *A01N 47/02* (2013.01); *A01N 49/00* (2013.01); *A61K 9/0017* (2013.01); *A61K 31/231* (2013.01); *A61K 31/4015* (2013.01); *A61K 31/4402* (2013.01); *A61K 45/06* (2013.01); *A61K 47/10* (2013.01); *A61K 47/22* (2013.01); *A61K 47/26* (2013.01); *A61K 47/32* (2013.01); *A61P 33/14* (2018.01); *A61K 2300/00* (2013.01)

(58) Field of Classification Search
CPC .. A61K 31/415; A61K 31/231; A61K 9/0017; A61P 33/14
See application file for complete search history.

(56) References Cited

U.S. PATENT DOCUMENTS

| | | |
|---|---|---|
| 6,096,329 A | 8/2000 | Jeannin |
| 2009/0312387 A1 | 12/2009 | Sirinyan et al. |
| 2010/0016398 A1 | 1/2010 | Sirinyan et al. |
| 2010/0311685 A1 | 12/2010 | Derrieu |
| 2011/0060023 A1 | 3/2011 | Donnelly |
| 2011/0071193 A1 | 3/2011 | Nouvel |
| 2011/0245191 A1 | 10/2011 | Rosentel |
| 2011/0288141 A1 | 11/2011 | Freehauf et al. |
| 2012/0071484 A1 | 3/2012 | Reynolds |
| 2013/0065930 A1 | 3/2013 | Malhotra et al. |
| 2013/0225516 A1 | 8/2013 | Soli et al. |
| 2013/0261161 A1 | 10/2013 | Preston et al. |
| 2014/0194475 A1 | 7/2014 | Ecker |

FOREIGN PATENT DOCUMENTS

| | | |
|---|---|---|
| CN | 103355324 A | 10/2013 |
| GB | 2457734 A | 8/2009 |
| GB | 2464449 A | 4/2010 |
| WO | 2011/038024 A1 | 3/2011 |
| WO | 2016/069983 A1 | 5/2016 |

*Primary Examiner* — Shobha Kantamneni
(74) *Attorney, Agent, or Firm* — John Ezcurra (57) ABSTRACT

The present invention relates to various topical veterinary compositions comprising fipronil, an insect growth regulator, and a veterinarily acceptable carrier.

5 Claims, 1 Drawing Sheet

VETERINARY FORMULATIONS

CROSS REFERENCE TO RELATED APPLICATIONS

This application is the national stage application of International Patent Application No. PCT/US2016/062364 filed on Nov. 16, 2016, which claims the benefit of priority to United Kingdom patent application no. 15207244 filed on Nov. 24, 2015, which is incorporated herein by reference in its entirety.

The present invention relates to topical veterinary formulations for controlling ectoparasites, in particular fleas and ticks, on animals. More particularly, the invention relates to topical formulations comprising a 1-N-phenylpyrazole (fipronil) and a second active which is an insect growth regulator (IGR) and a veterinarily acceptable liquid carrier. The invention further relates to methods and uses of said formulations in eradicating, controlling and preventing parasite infestation in animals.

BACKGROUND TO THE INVENTION

Animals such as mammals and birds are often susceptible to parasite infestations/infections. These parasites may be ectoparasites, such as insects, and endoparasites such as filariae and other worms. Domesticated animals, such as cats and dogs, are often infested with one or more of the following ectoparasites: fleas (*Ctenocephalides* spp., such as *Ctenocephalides felis* and the like), ticks (*Rhipicephalus* spp., *Ixodes* spp., *Dermacentor* spp., *Amblyoma* spp., and the like), mites (*Demodex* spp., *Sarcoptes* spp., *Otodectes* spp., and the like), lice (*Trichodectes* spp., *Cheyletiella* spp., *Lignonathus* spp. and the like), mosquitoes (*Aedes* spp., *Culux* spp., *Anopheles* spp. and the like) and flies (*Hematobia* spp., *Musca* spp., *Stomoxys* spp., *Dematobia* spp., *Coclyomia* spp. and the like).

Fleas are a particular problem because not only do they adversely affect the health of the animal or human, but they also cause a great deal of psychological stress. Moreover, fleas are also vectors of pathogenic agents in animals, such as dog tapeworm (*Dipylidium caninum*), and humans.

Similarly, ticks are also harmful to the physical and psychological health of the animal or human. However, the most serious problem associated with ticks is that they are the vector of pathogenic agents in both humans and animals. Major diseases which are caused by ticks include borrelioses (Lyme disease caused by *Borrelia burgdorferi*), babesioses (or piroplasmoses caused by *Babesia* spp.) and rickettsioses (also known as Rocky Mountain spotted fever). Ticks also release toxins which cause inflammation or paralysis in the host. Occasionally, these toxins are fatal to the host.

Moreover, mites and lice are particularly difficult to combat since there are very few active substances which act on these parasites and they require frequent treatment.

Likewise, farm animals are also susceptible to parasite infestations. For example, cattle are affected by a large number of parasites. A parasite which is very prevalent among farm animals is the tick genus *Boophilus*, especially those of the species microplus (cattle tick), *decoloratus* and *annulatus*. Ticks, such as *Boophilus microplus*, are particularly difficult to control because they live in the pasture where farm animals graze. Other important parasites of cattle and sheep are listed as follows: myiases-causing flies such as *Dermatobia hominis* (known as Berne in Brazil) and *Cochlyomia hominivorax* (greenbottle); sheep myiases-causing flies such as *Lucilia sericata, Lucilia cuprina* (known as blowfly strike in Australia, New Zealand and South Africa). These are flies whose larva constitutes the animal parasite; flies proper, namely those whose adult constitutes the parasite, such as *Haematobia irritans* (horn fly); lice such as *Linognathus vitulorum*, etc.; and mites such as *Sarcoptes scabiei* and *Psoroptes ovis*.

1-Arylpyrazoles are a class of chemicals well known in the art, and certain compounds in this class have been found to be potently active against a wide range of pests and parasites that are harmful to animals and plants. For example, 1-arylpyrazole derivatives are known in the art to prevent, treat or control ectoparasitic infestations in mammals, such as cats, dogs and cattle. Certain 1-arylpyrazoles and their use against pests are described in US Patent Publication Nos. US 2005/0182048; US 2006/0135778; US 2008/0132487; US 2008/0031902; U.S. Pat. Nos. 4,963,575; 5,122,530; 5,232,940; 5,236,938; 5,246,255; 5,547,974; 5,567,429; 5,576,429; 5,608,077; 5,714,191; 5,814,652; 5,885,607; 5,567,429; 5,817,688; 5,885,607; 5,916,618; 5,922,885; 5,994,386; 6,001,384; 6,010,710; 6,057,355; 6,069,157; 6,083,519; 6,090,751; 6,096,329; 6,124,339; 6,180,798; 6,335,357; 6,350,771; 6,372,774; 6,395,906; 6,413,542; 6,685,954; and 7,468,381. See also: EP 0 234 119, EP 0 295 117, EP 0 352 944, EP 0 500 209, EP 0 780 378, EP 0 846 686, and EP 0 948 485, all of which are incorporated herein by reference in their entirety. A novel class of 1-N-arylpyrazole-based insecticides has been described in patents EP295217 and EP352944. The compounds of the classes defined in these patents are highly active, and one of these compounds (1-(2,6-$Cl_2$-4-$CF_3$phenyl)-3-CN-4-(SO—$CF_3$)-5-$NH_2$pyrazole), whose common name is fipronil, has proven to be highly effective against mammal ectoparasites and in particular, but not exclusively, fleas, ticks, flies and myiases. Fipronil is the active ingredient in the commercial veterinary products FRONTLINE® and FRONTLINE® Plus.

The class of acaricides or insecticides known as insect growth regulators (IGRs) is well known to the practitioner and represents a wide range of different chemical classes. These compounds all act by interfering with the development or growth of the insect pests. Insect growth regulator compounds typically act either by blocking the development of the immature stages (eggs and larvae) into adult stages, or by inhibiting the synthesis of chitin. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329, 6,685,954 and 5,439,924 (all incorporated herein by reference).

Combinations comprising a 1-N-arylpyrazole and an IGR are already well known in the art. For example, U.S. Pat. No. 6,096,329 (incorporated by reference) describes a spot-on composition for the long lasting protection against fleas and ticks on mammals which comprises fipronil, a compound which mimics juvenile hormones and at least one customary spot-on formulation adjuvant. In addition to the two actives, the spot-on compositions described in U.S. Pat. No. 6,096,329 advantageously comprise a crystallization inhibitor, an organic solvent having a dielectric constant of between 10 and 35, and an organic co-solvent having a boiling point of below 100° C. and a dielectric constant of between 10 and 40. The co-solvent is volatile and serves as a drying promoter, whilst the crystallisation inhibitor prevents precipitation of the actives out of solution, which can often be problematic in low volume-high concentration solutions.

Spot-on formulations are capable of topically delivering an antiparasitic agent to a limited area of the host. For example, U.S. Pat. Nos. 5,045,536, 426,333; 6,482,425; 6,962,713; and 6,998,131, all incorporated herein by reference, describe spot-on formulations. WO 01/95715, also incorporated herein by reference, describes a method for controlling ectoparasites in small rodents as well as interrupting or preventing the diseases caused by arthropods or small rodents, which comprise applying topical formulations, such as spot-on compositions, to the skin, or hair of the rodents.

Spot-on formulations are typically applied to a localized region of the animal's skin, usually in one or two spots between the animal's shoulder blades. Once applied, the actives distribute over the animal's whole body from the point of application. Cochet and co-workers reported the distribution of fipronil to the stratum corneum, the viable epidermis and the sebaceous glands and epithelial layers of beagle dogs after spot-on administration (see Cochet et al., Eur. J. Drug Metab. Pharmacokinet., 1997, 22(3), 211-216). Using $^{14}C$ radiolabeled drug, the publication demonstrated that fipronil is displaced from the point of application and distributed to the whole skin, where it was persistently detected for up to 56 days after treatment. The benefits of spot-on application, in terms of both efficacy and ease of application, are reflected in the commercial success of FRONTLINE® Plus, a spot-on formulation comprising fipronil and methoprene, which has been a worldwide leading veterinary product for many years.

The present invention seeks to provide alternative and/or improved topical formulations comprising fipronil in combination with an IGR.

STATEMENT OF INVENTION

A first aspect of the invention relates to a topical formulation comprising:
(i) fipronil;
(ii) an IGR;
(iii) optionally one or more antioxidants; and
(iv) an organic solvent which is an optionally substituted pyrrolidone;
wherein said formulation does not contain an organic co-solvent having a boiling point of below 100° C. and a dielectric constant of between 10 and 40; or
wherein said formulation does not contain a crystallisation inhibitor.

A second aspect of the invention relates to a topical formulation comprising:
(i) fipronil;
(ii) methoprene;
(iii) optionally one or more antioxidants; and
(iv) an organic solvent which is an optionally substituted pyrrolidone.

A third aspect of the invention relates to a topical formulation comprising:
(i) fipronil;
(ii) pyriproxyfen;
(iii) optionally one or more antioxidants; and
(iv) an organic solvent which is an optionally substituted pyrrolidone.

A fourth aspect of the invention relates to a topical formulation comprising:
(i) fipronil in an amount of from about 10 to about 20% w/v;
(ii) an IGR in an amount of from about 10 to about 20% w/v;
(iii) optionally one or more antioxidants; and
(iv) an organic solvent which is glycol ether;
wherein said formulation does not contain an organic co-solvent having a boiling point of below 100° C. and a dielectric constant of between 10 and 40; or
wherein said formulation does not contain a crystallisation inhibitor.

A fifth aspect of the invention relates to a topical formulation comprising:
(i) fipronil;
(ii) an IGR;
(iii) optionally one or more antioxidants; and
(iv) an organic solvent which is a glycol ether selected from methyl diglycol, ethyl diglycol, propyl diglycol, butyl diglycol, methyl glycol, ethyl glycol, dipropylene glycol n-butyl ether, ethylene glycol monoethyl ether, ethylene glycol monomethyl ether, dipropylene glycol monomethyl ether, diethylene glycol monobutyl ether, diethylene glycol monomethyl ether, ethylene glycol monobutyl ether, propylene glycol monomethyl ether, and mixtures thereof;
wherein said formulation does not contain an organic co-solvent having a boiling point of below 100° C. and a dielectric constant of between 10 and 40; or
wherein said formulation does not contain a crystallisation inhibitor.

A sixth aspect of the invention relates to a topical formulation comprising:
(i) fipronil;
(ii) pyriproxyfen;
(iii) optionally one or more antioxidants; and
(iv) an organic solvent which is glycol ether;
wherein said formulation does not contain an organic co-solvent having a boiling point of below 100° C. and a dielectric constant of between 10 and 40; or
wherein said formulation does not contain a crystallisation inhibitor.

A seventh aspect of the invention relates to a topical formulation as described above for use in treating or controlling ectoparasites on an animal.

An eighth aspect of the invention relates to a method of treating or controlling ectoparasites on an animal, said method comprising topically applying a topical composition as described above.

Formulations according to the invention have been shown to exhibit excellent efficacy against fleas, both in terms of duration of efficacy and their effect on inhibition of egg hatching. Moreover, certain embodiments of the invention offer one or more additional advantages, including but not limited to, simplicity (fewer components), ease of formulation and/or improved efficacy. The spot-on formulations according to the invention are particularly advantageous owing to their efficacy, the speed of action and the pleasant appearance of the animal's fur after application and drying.

DETAILED DESCRIPTION

Aspects of the invention and further preferred embodiments are presented in the accompanying claims and numbered paragraphs.

In this disclosure and in the claims, terms such as "comprises," "comprising," "containing" and "having" and the like can mean "includes," "including," and the like. The term "consisting essentially of" or "consists essentially" is open-ended, allowing for the presence of more than that which is recited so long as basic or novel characteristics of that which is recited is not changed by the presence of more than that which is recited, but excludes prior art embodiments.

Certain embodiments of the invention relate to topical formulations that do not contain an organic co-solvent, wherein said organic co-solvent has a boiling point of below 100° C. and a dielectric constant of between 10 and 40. Typically, prior art spot-on formulations comprise an organic co-solvent to aid dissolution of the actives, and also act as a drying promoter.

Examples of co-solvents falling within this definition include absolute ethanol, methanol and isopropanol.

Thus, in certain preferred embodiments, the invention relates to formulations that do not contain ethanol, methanol or isopropanol.

Surprisingly, studies by the applicant have demonstrated that the presence of a co-solvent is not critical in spot-on formulations. In fact, studies by the applicant have demonstrated that certain formulations which lack a co-solvent actually exhibit comparable duration of efficacy with that of the commercial product Frontline® Plus. For example, this is observed for formulations where the solvent is a glycol ether (e.g. DGME), or an optionally substituted pyrrolidone (e.g. NMP). Further details of these studies are set forth in the accompanying examples.

Other embodiments of the invention relate to topical compositions that do not contain a crystallisation inhibitor.

As used herein, the term "crystallisation inhibitor" refers to a compound that is capable of inhibiting precipitation of the actives (e.g. fipronil and/or the IGR, where the IGR is a solid at room temperature) from the veterinarily acceptable carrier.

The skilled person would be familiar with the use of crystallisation inhibitors in topical compositions, particularly in the context of high concentration-low volume compositions such as spot-on compositions. Crystallisation inhibitors are typically used in an amount of from about 1 to about 20% (w/v), preferably from about 5 to about 15% w/v.

In certain preferred embodiments of the invention, the formulation is completely free from crystallisation inhibitor.

Typically, the skilled person would be able to identify suitable crystallization inhibitors by way of a simple laboratory test. By way of illustration, one non-limiting example of such a simple laboratory test is set out as follows: 0.3 ml of a solution of fipronil is added to the veterinarily acceptable carrier along with 10% of the purported crystallisation inhibitor, and the mixture is deposited on a glass slide at 20° C. and left for 24 hours, after which it is observed with the naked eye whether there are crystals present. If the compound satisfies the test, there will be fewer than 10 crystals, preferably less than 5 crystals, even more preferably, zero crystals on the glass slide. Typically, the skilled person would carry out the test under standard laboratory conditions (e.g. in a weighing cabinet or similar such apparatus to avoid excessive air flow or variable conditions during the test).

Suitable crystallisation inhibitors in the context of the present invention include, but are not limited to the following:

polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, acrylic derivatives such as methacrylates and the like, anionic surfactants such as alkaline stearates, in particular sodium, potassium or ammonium stearate; calcium stearate; triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil, cationic surfactants such as water-soluble quaternary ammonium salts of formula N+R'R"R'''R'''',Y— in which the radicals R are optionally hydroxylated hydrocarbon radicals and Y— is an anion of a strong acid such as the halide, sulphate and sulphonate anions; cetyltrimetylammonium bromide is among the cationic surfactants 9 an be used, amine salts of formula N+R'R'XR''' in which the radicals R are optionally hydroxylated hydrocarbon radicals; octadecylamine hydrochloride is among the cationic surfactants which can be used, nonionic surfactants such as optionally polyoxyethylenated sorbitan esters, in particular polysorbate 80, polyoxyethylenated alkyl ethers; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, amphoteric surfactants such as substituted lauryl compounds of betaine, or preferably a mixture of at least two of these crystallization inhibitors.

In certain preferred embodiments of the invention, the formulation is completely free from the above-recited compounds listed as crystallisation inhibitors.

In certain preferred embodiments, the formulation contains less than about 1% w/v of one or more of the above-mentioned compounds listed as crystallisation inhibitors, more preferably, less than about 0.5% w/v, even more preferably, less than about 0.1% w/v, more preferably still, less than about 0.05% or 0.01% w/v of the formulation.

Advantageously, clinical studies by the applicant have demonstrated that spot-on formulations according to the invention which lack a crystallisation inhibitor exhibit surprisingly good duration of efficacy against fleas. This is observed where the solvent is a glycol ether (e.g. DGME), or an optionally substituted pyrrolidone (e.g. NMP). Further details of these studies are set forth in the accompanying examples.

In certain particularly preferred embodiments of the invention, the formulations lack both an organic co-solvent, wherein said organic co-solvent has a boiling point of below 100° C. and a dielectric constant of between 10 and 40, and a crystallisation inhibitor as desribed above.

Thus, in certain particularly preferred embodiments of the invention, the formulations do not contain a crystallisation inhibitor as described above, nor do they contain ethanol, methanol or isopropanol.

In one embodiment, the formulations comprise a crystallisation inhibitor as described above, but do not comprise a co-solvent as described above.

In one embodiment, the formulations comprise a co-solvent as described above, but do not comprise a crystallisation inhibitor as described above.

In certain highly preferred embodiments, the formulations consist essentially of, or consist of, fipronil, an IGR, and a veterinarily acceptable carrier which is an optionally substituted pyrrolidone or a glycol ether, and optionally one or more antioxidants.

In other embodiments, the formulations may contain fipronil, an IGR and one or more additional active agents in a veterinarily acceptable carrier.

Insect Growth Regulators

The compositions of the invention contain one or more insect growth regulators (IGRs). In one embodiment, the IGR is a compound which mimics juvenile hormones. Suitable examples include:
azadirachtin (Agridyne);
diofenolan (Ciba Geigy);
fenoxycarb (Ciba Geigy);
hydroprene (Sandoz);
kinoprene (Sandoz);
methoprene (Sandoz);
pyriproxyfen (Sumitomo/Mgk);
tetrahydroazadirachtin (Agridyne); and
4-chloro-2-(2-chloro-2methylpropyl)-5-(6-iodo-3-pyridylmethoxy)pyridazin-3(2H)-one.

In another embodiment, the IGR is a chitin-synthesis inhibitor. Suitable examples include:
chlorfluazuron (Ishihara Sangyo);
cyromazine (Ciba Geigy);
diflubenzuron (Solvay Duphar);
fluazuron (Ciba Geigy);
flucycloxuron (Solvay Duphar);
flufenoxuron (Cyanamid);
hexaflumuron (Dow Elanco);
lufenuron (Ciba Geigy);
tebufenozide (Rohm & Haas);
teflubenzuron (Cyanamid); and
triflumuron (Bayer).

The above compounds are defined by their international common name (The Pesticide Manual, 10th edition, 1994, Ed. Clive Tomlin, Great Britain).

As chitin-synthesis inhibitors, mention may also be made of compounds such as 1-(2,6-difluorobenzoyl)-3-(2-fluoro-4-(trifluoromethyl)phenylurea, 1-(2,6-difluorobenzoyl)-3-(2-fluoro-4-(1,1,2,2-tetrafluoroethoxy)phenylurea and 1-(2,6-difluorobenzoyl)-3-(2-fluoro-4-trifluoromethyl) phenylurea. Novaluron (Isagro, Italian company) may also be mentioned as an IGR.

In certain preferred embodiments, the IGR is selected from cyromazine, lufenuron, 1-(2,6-difluorobenzoyl)-3-(2-fluoro-4-(trifluoromethyl)phenylurea, azadirachtin, diofenolan, fenoxycarb, hydroprene, kinoprene, methoprene, pyriproxyfen, tetrahydroazadirachtin and 4-chloro-2-(2-chloro-2methylpropyl)-5-(6-iodo-3-pyridylmethoxy)pyridizin-3(2H)-one In certain highly preferred embodiments, the IGR is methoprene, more preferable S-methoprene.

In certain other embodiments, the IGR is pyriproxyfen.

In certain preferred embodiments, the IGR is present in an amount of from about 1 to about 20% (w/v).

In certain more preferred embodiments, the IGR is present in an amount of from about 5 to about 15% (w/v), more preferably from about 8 to about 12% (w/v), even more preferably from about 9 to about 11% (w/v).

Fipronil

The formulations of the present invention all contain fipronil, the compound known as (1-(2,6-Cl$_2$-4-CF$_3$phenyl)-3-CN-4-(SO—CF$_3$)-5-NH$_2$pyrazole).

Fipronil and related compounds may be prepared according to one or other of the processes described in patent applications WO-A-87/3781, 93/6089, 94/21606 or European patent application EP-A-0,295,117, or any other process which falls within the competence of a specialist skilled in the art of chemical synthesis.

In certain preferred embodiments of the invention, the fipronil is present in an amount of from about 1 to about 20% (w/v).

Preferably, the fipronil is present in an amount of from about 5 to about 15% (w/v), more preferably from about 8 to about 12% (w/v), even more preferably from about 9 to about 11% (w/v).

The proportions, by weight, of compounds of fipronil and the IGR are preferably between 80/20 and 20/80.

Additional Active Agents

In another embodiment of the invention, one or more macrocyclic lactones, which act as an acaricide, an anthelmintic agent and/or an insecticide, can be included in the compositions of the invention. For the avoidance of doubt, the term "macrocyclic lactone" as used herein includes both naturally occurring and synthetic or semi-synthetic avermectin and milbemycin compounds.

The macrocyclic lactones that may be used in the compositions of the invention include, but are not limited to, the naturally produced avermectins (e.g. including the components designated as $A_1a$, $A_1b$, $A_2a$, $A_2b$, $B_1a$, $B_1b$, $B_2a$ and $B_2b$) and milbemycin compounds, semisynthetic avermectins and milbemycins, avermectin monosaccharide compounds and avermectin aglycone compounds. Examples of macrocyclic lactone compounds that may be used in the compositions include, but are not limited to, abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin $A_3$, milbemycin $A_4$, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054, both incorporated herein by reference.

The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, New Jersey (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054, all incorporated herein by reference.

In one embodiment, the veterinary compositions of the invention may comprise an effective amount of at least one of abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin or nemadectin, or a combination thereof. In another embodiment, the invention provides a veterinary composition comprising an effective amount of at least one of abamectin, emamectin, eprinomectin, ivermectin, doramectin or selamectin, or a combination thereof. In still another embodiment, the veterinary compositions of the invention comprise an effective amount of at least one of ivermectin, milbemectin, milbemycin oxime or moxidectin, or a combination thereof.

In some embodiments, the compositions of the invention may include one or more antinematodal agents including, but not limited to, active agents in the benzimidazoles, imidazothiazoles, tetrahydropyrimidines and the organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions of the invention may include an imidazothiazole compounds including, but not limited to, tetramisole, levamisole and butamisole.

In still other embodiments, the compositions of the invention may include tetrahydropyrimidine active agents including, but not limited to, pyrantel, oxantel, and morantel.

Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, nitroxynil, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin, paromomycin II, praziquantel and epsiprantel.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a (4H)-dibenzofurancarboxaldehyde (MGK-11), 2-(2-ethylhexyl)-3a,4,7,7a-tetrahydro-4,7-methano-1H-isoindole-1,3 (2H)dione (MGK-264), dipropyl-2,5-pyridinedicarboxylate (MGK-326) and 2-(octylthio)ethanol (MGK-874).

In another embodiment, an antiparasitic agent that can be included in the veterinary compositions of the invention is a biologically active peptide or protein including, but not limited to, depsipeptides other than the compounds of formula (I). These include PF1022A or analogs thereof and emodepside. These compounds act at the neuromuscular junction by stimulating presynaptic receptors belonging to the secretin receptor family resulting in the paralysis and death of parasites. In one embodiment of the depsipeptide, the depsipeptide is emodepside (see Wilson et al., *Parasitology*, January 2003, 126(Pt 1):79-86).

In another embodiment, the compositions of the invention may comprise an active agent from the neonicotinoid class of parasiticides. The neonicotinoids bind and inhibit insect specific nicotinic acetylcholine receptors. In one embodiment, the neonicotinoid insecticidal agent is imidacloprid. Agents of this class are described, for example, in U.S. Pat. No. 4,742,060 or in EP 0 892 060 (both incorporated herein by reference). In another embodiment, the compositions of the invention may comprise nitenpyram, another active agent of the neonicotinoid class of pesticides. The use of nitenpyram for controlling fleas is described in U.S. Pat. No. 5,750,548, which is incorporated herein by reference in its entirety.

In certain other embodiments of the invention, the compositions of the invention may include a semicarbazone active agent, such as metaflumizone.

In another embodiment, the compositions of the invention may advantageously include one or more other isoxazoline compounds known in the art, including, but not limited to, afoxolaner, sarolaner and fluralaner. This class of active agents are described in U.S. Pat. Nos. 7,964,204, 8,410,153, WO 2014/036056, US 2010/0254960 A1, US2011/0159107, US2012/0309620, US2012/0030841, US2010/0069247, WO 2007/125984, WO 2012/086462, U.S. Pat. Nos. 8,318, 757, 8,466,115, 8,618,126, 8,822,466, 8,383,659, 8,853,186, US 2011/0144349, U.S. Pat. Nos. 8,053,452; 8,952,175, US 2010/0254959, US 2011/152081, WO 2007/075459 and US 2009/0133319, WO 2009/025983 and U.S. Pat. No. 8,513, 431, WO 2009/003075 and US 2010/0173948, WO 2008/150393, WO 2008/154528 and U.S. Pat. No. 8,623,875, WO 2010/003877 and U.S. Pat. No. 8,597,688, WO 2010/003923 and U.S. Pat. No. 8,563,474, WO 2009/045999 and U.S. Pat. No. 8,367,584, WO 2009/126668 and U.S. Pat. No. 8,546,618, WO 2009/051956, WO 2012/089623, WO 2012/089622, U.S. Pat. Nos. 8,119,671; 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/

154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1, U.S. Pat. Nos. 7,897,630, and 7,951,828, all of which are incorporated herein by reference in their entirety.

In another embodiment of the invention, nodulisporic acid and its derivatives may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in U.S. Pat. No. 7,084,280 to Ducray et al. (incorporated herein by reference); Sager et al., Veterinary Parasitology, 2009, 159, 49-54; Kaminsky et al., Nature vol. 452, 13 Mar. 2008, 176-181.

The compositions of the invention may also include aryloazol-2-yl cyanoethylamino compounds such as those described in U.S. Pat. No. 8,088,801 to Soil et al., which is incorporated herein by reference, and thioamide derivatives of these compounds, as described in U.S. Pat. No. 7,964,621 to Le Hir de Fallois, which is also incorporated herein by reference. Aryloazol-2-yl cyanoethylamino active agents, which are systemically-acting against endoparasites, may be used in the veterinary compositions of the invention.

The compositions of the invention may also include paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tett. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432 and US 2010/0197624, U.S. Pat. Nos. 5,703,078 and 5,750,695, all of which are hereby incorporated by reference in their entirety.

In another embodiment of the invention, the compositions may include a spinosyn active agent produced by the soil actinomycete *Saccharopolyspora spinosa* (see, for example Salgado V. L. and Sparks T. C., "*The Spinosyns: Chemistry, Biochemistry, Mode of Action, and Resistance*," in Comprehensive Molecular Insect Science, vol. 6, pp. 137-173, 2005) or a semi-synthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the invention. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by *Saccharopolyspora pagona*, which may be used in the compositions of the invention, may be produced via fermentation by conventional techniques known in the art. Other spinosyn compounds that may be used in the compositions of the invention are disclosed in U.S. Pat. Nos. 5,496,931; 5,670,364; 5,591,606; 5,571,901; 5,202,242; 5,767,253; 5,840,861; 5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In general, additional active agents (other than fipronil and an IGR) are included in the dosage units of the invention in an amount of between about 0.1 µg and about 1000 mg. Typically, the active agent may be included in an amount of about 10 µg to about 500 mg, about 10 µg to about 400 mg, about 1 mg to about 300 mg, about 10 mg to about 200 mg or about 10 mg to about 100 mg. More typically the additional active agent will be present in an amount of about 5 mg to about 50 mg in the compositions of the invention.

The concentration of the additional active agent in the compositions of the invention will typically be from about 0.01% to about 30% (w/w) depending on the potency of the active agent. In certain embodiments for very potent active agents including, but not limited to a macrocyclic lactone active agent, the concentration of the active agent will typically be from about 0.01% to about 10% (w/w), from about 0.01 to about 1% (w/w), from about 0.01% to about 0.5% (w/w), from about 0.1% to about 0.5% (w/w) or from about 0.01% to about 0.1% (w/w). In other embodiments, the concentration of the active agent will typically be from about 0.1% to about 2% (w/w) or about 0.1% to about 1% (w/w).

Other Components

In certain preferred embodiments of the invention, the formulation further comprises one or more antioxidants.

Preferably, the total amount of antioxidant present is from about 0.005 to about 1% (w/v), more preferably from about 0.01 to about 0.05% (w/v).

Preferably, the antioxidant is selected from butylhydroxyanisole, butylhydroxytoluene, ascorbic acid, sodium metabisulphite, propyl gallate and sodium thiosulphate, and mixtures thereof. More preferably, the antioxidant is butylhydroxyanisole, butylhydroxytoluene, or a mixture thereof.

Salts/Esters

The active ingredients of the invention can be present as salts or esters, in particular pharmaceutically and veterinarily acceptable salts or esters.

Pharmaceutically acceptable salts of the active ingredients of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the active ingredients of the invention. The person skilled in the art will recognise active ingredients that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Active ingredients of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the active ingredients of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those active ingredients, and mixtures thereof. The terms used in the claims encompass these forms, provided said forms retain the appropriate functional activity (though not necessarily to the same degree).

The present invention also includes all suitable isotopic variations of the active ingredient or a pharmaceutically acceptable salt thereof. An isotopic variation of an active ingredient of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$ $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. For example, the invention includes active ingredients where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Solvates and Polymorphs

The present invention also includes solvate forms of the active ingredients of the present invention. The terms used in the claims encompass these forms.

The invention further relates to the active ingredients of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such active ingredients.

Veterinarily Acceptable Carrier

The formulations of the invention comprise a liquid veterinarily acceptable carrier. One aspect of the invention relates to formulations where the carrier is an optionally substituted pyrrolidone.

In certain preferred embodiments, the optionally substituted pyrrolidone is selected from 2-pyrrolidone, a 1-($C_{2-20}$-alkyl)-2-pyrrolidone, a 1-($C_{2-10}$-alkenyl)-2-pyrrolidone, a 1-($C_{3-8}$-cycloalkyl)-2-pyrrolidone, a 1-($C_{1-6}$-hydroxyalkyl)-2-pyrrolidone, a 1-($C_{1-6}$-alkoxy-$C_{1-6}$alkyl)-2-pyrrolidone and 1-benzylpyrrolidone.

In certain more preferred embodiments, the optionally substituted pyrrolidone is selected 1-methylpyrrolidone (NMP), 1-ethylpyrrolidone, 1-octylpyrrolidone, 1-dodecylpyrrolidone, 1-isopropylpyrrolidone, 1-(s-butyl)-pyrrolidone, 1-(t-butyl)-pyrrolidone, 1-(n-butyl)-pyrrolidone, 1-hexylpyrrolidone, 1-vinyl-2-pyrrolidone, 1-cyclohexylpyrrolidone, 1-(2-hydroxyethyl)-pyrrolidone, 1-(3-hydroxypropyl)-pyrrolidone, 1-(2-methoxyethyl)-pyrrolidone, 1-(3-methoxypropyl)-pyrrolidone and 1-benzylpyrrolidone, and mixtures thereof.

In certain highly preferred embodiments, the optionally substituted pyrrolidone is N-methylpyrrolidone (NMP).

Another aspect of the invention relates to compositions where the carrier is a glycol ether.

Preferably, the glycol ether is an alkyl ether of ethylene glycol or propylene glycol or an alkyl ether of a polyethylene or polypropylene glycol.

In certain preferred embodiments, the glycol ether is selected from methyl diglycol, ethyl diglycol, propyl diglycol, butyl diglycol, methyl glycol, ethyl glycol, dipropylene glycol n-butyl ether, ethylene glycol monoethyl ether, ethylene glycol monomethyl ether, dipropylene glycol monomethyl ether, diethylene glycol monoethyl ether (DGME), diethylene glycol monobutyl ether, diethylene glycol monomethyl ether, ethylene glycol monobutyl ether, propylene glycol monomethyl ether, and mixtures thereof.

In other certain preferred embodiments, the glycol ether is selected from methyl diglycol, ethyl diglycol, propyl diglycol, butyl diglycol, methyl glycol, ethyl glycol, dipropylene glycol n-butyl ether, ethylene glycol monoethyl ether, ethylene glycol monomethyl ether, dipropylene glycol monomethyl ether, diethylene glycol monobutyl ether, diethylene glycol monomethyl ether, ethylene glycol monobutyl ether, propylene glycol monomethyl ether, and mixtures thereof.

In one particularly preferred embodiment, the glycol ether is diethylene glycol monoethyl ether (DGME). DGME is available commercially as Transcutol® (Gattefosse).

Although it is not preferred, the spot-on formulation may optionally comprise water, in particular in a proportion of form 0 to 30% (volume per unit volume, V/V), in particular from 0 to 5%.

The formulations for topical application according to the invention are typically prepared by simple mixing of the active materials with the veterinarily acceptable carrier, followed by addition of any other ingredients or adjuvants (e.g. antioxidants).

The formulations according to the invention are primarily intended for pets, in particular cats and dogs, and are generally applied by being deposited onto the skin ("spot-on" or "pour-on" application).

The formulation according to the invention may be in the form of a concentrated emulsion, suspension or solution. Preferably, the formulation is a solution.

Spot-on Formulations

In one preferred embodiment of the invention, the formulation is in the form of a spot-on formulation. Spot-on formulations are applied to a localized area of the skin, typically an area of less than 10 cm$^2$, more typically between 5 and 10 cm$^2$. Typically, the spot-on formulation is applied two points, preferably localized between the animal's shoulders. Once deposited, the active ingredients diffuse over the animal's entire body.

Typically, the volume of spot-on formulation applied may be from about 0.3 to 5 ml, preferably about 0.5 ml for cats, and from about 0.3 to 5 ml for dogs, according to the weight of the animal.

Pour-on Formulations

In an alternative, but less preferred embodiment, the formulation of the invention is in the form of a pour-on formulation.

Pour-on formulations are typically poured along the dorsal midline of the animal (usually livestock animals). The volume of pour-on formulation applied is typically greater than that for a spot-on formulation and is generally in the order of about 5 ml to about 50 ml, or about 10 ml to about 100 ml, according to the weight of the animal.

Efficacy

Formulations of the invention have applications in the treatment and prevention of parasitoses having pathogenic consequences. More specifically, the formulations are for use in controlling ectoparasites, in particular ticks and/or fleas.

Formulations according to the invention, in particular those for spot-on application, have proven to be extremely effective for the very long-lasting treatment of fleas on mammals, and, in particular, small mammals such as cats and dogs.

The very high efficacy of the formulations according to the invention implies not only high immediate efficacy but also very long-lasting efficacy after the animal has been treated.

For the purposes of the present invention, the term flea is understood to refer to all the usual or accidental species of parasitic flea of the order Siphonaptera, and in particular the species *Ctenocephalides*, in particular *C. felis* and *C. canis*, rat fleas (*Xenopsylla cheopis*) and human fleas (*Pulex irritans*).

The formulations of the invention are effective against ectoparasites such as insects or arachnids including those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Damalinia, Linognathus, Haematopinus, Solenoptes, Trichodectes*, and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include but are not limited to cat and dog fleas (*Ctenocephalides felis, Ctenocephalides* spp. and the like), ticks (*Rhipicephalus* spp., *Ixodes* spp., *Dermacentor* spp., *Amblyoma* spp. and the like), and mites (*Demodex* spp., *Sarcoptes* spp., *Otodectes* spp. and the like), lice (*Trichodectes* spp., *Cheyletiella* spp., *Lignonathus* spp., and the like), mosquitoes (*Aedes* spp., *Culex* spp., *Anopheles* spp., and the like) and flies (*Hematobia* spp., *Musca* spp., *Stomoxys* spp., *Dematobia* spp., *Cochliomyia* spp., and the like). In yet another embodiment for the treatment against ectoparasites, the ectoparasite is a flea and/or tick.

Additional examples of ectoparasites that are controlled by the formulations of the invention include but are not limited to the tick genus *Boophilus*, especially those of the species *microplus* (cattle tick), *decoloratus* and *annulatus*; myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabici* and *Psoroptes ovis*. The above list is not exhaustive and other ectoparasites are well known in the art to be harmful to animals and humans. These include, for example migrating dipterous larvae.

Dosage

A person of ordinary skill in the art can easily determine an appropriate dose of one of the instant formulations to administer to an animal without undue experimentation. Typically, a veterinarian will determine the actual dosage which will be most suitable for an individual patient and it will depend on a variety of factors including the activity of the specific active ingredients employed, the metabolic stability and length of action of those active ingredients, the age, body weight, general health, sex, diet, mode and time of administration, rate of excretion, drug combination, the severity of the particular condition, and the subject undergoing treatment. The dosages disclosed herein are exemplary of the average case. There can of course be individual instances where higher or lower dosage ranges are merited, and such are within the scope of this invention.

It is preferable for the formulation of the invention to be applied to the animal every two or, preferably, every three months on cats and dogs.

Preferably, the treatment is carried out so as to administer to the animal a dose of from 0.1 to 40 and in particular from 1 to 20 mg/kg of fipronil and a dose of from 0.1 to 40 and in particular 1 to 30 mg/kg of the IGR.

The preferred doses are from 5 to 15 mg/kg for fipronil and from 0.5 to 15 mg/kg or 10 to 20 mg/kg for the IGR.

It is understood that the dosage values which are thus indicated are average values which may vary within a wide range, since, in practice, a formulation having defined doses of fipronil and of the IGR will be administered to animals having relatively different weights. Consequently, the doses actually applied are often smaller or larger by a factor which may be up to 2, 3 or 4 relative to the preferred dose, without entailling any toxic risk for the animal in the case of an overdose, and while at the same time retaining real efficacy, possibly of shorter duration, in the case of an underdose.

The volume applied may be from about 0.3 to 1 ml, preferably about 0.5 ml for cats, and from about 0.3 to 5 ml for dogs, according to the weight of the animal.

Advantageously, the ready-to-use composition contains a dose of from 0.1 to 40 mg/kg of fipronil, and 0.1 to 40 mg/kg of the IGR.

Preferably, a ready-to-use dosed formulation, in particular one for spot-on application, contains 1 to 20 mg/kg, preferably 2 to 10 mg/kg of fipronil, and from 1 to 30 mg/kg, preferably 2 to 10 mg/kg, or 10 to 20 mg/kg of the IGR.

The present invention is further described by way of the following non-limiting examples and FIGURES, wherein.

EXAMPLES

Efficacy of Four Formulations of Fipronil and (S)-Methoprene Against Fleas (Ctenocephalides felis) on Dogs The efficacy of four different formulations of fipronil and (S)-methoprene was evaluated against adult flea (Ctenocephalidis felis) infestations on dogs when compared to untreated controls. In addition, the effect of the combination on flea egg eclosion was also determined.

Forty-four dogs (22 males and 22 females) were used in the study weighing 5.3 to 13.8 kg.

This study was a negative controlled, single-site, clinical efficacy study using a randomized block design with blocks based on pre-treatment live flea counts within sex. Within blocks, dogs were randomly allocated to one of five treatment groups:

Treatment Group 1: untreated control
Treatment Group 2:
Commercial formulation—FRONTLINE® Plus Spot-on
10% w/v fipronil
9% w/v (S)-methoprene
Treatment Group 3:
Topical spot-on
10% w/v fipronil
10% w/v (S)-methoprene
QS diethylene glycol monoethyl ether (DGME)
Treatment Group 4:
Topical spot-on
10% w/v fipronil
10% w/v (S)-methoprene
QS N-methyl pyrrolidone (NMP)
Treatment Group 5
Topical Spot-on
10% w/v fipronil
10% w/v (S)-methoprene
5% (w/v) polyvinylpyrrolidone (PVP) Kollidon 17
5% (w/v) polysorbate 80
QS diethylene glycol monoethyl ether (DGME)

Dogs in Treatment Group 1 were untreated while dogs in Groups 2-5 were each treated on Day 0 with 0.1 mL/kg body weight of the appropriate formulation containing fipronil and (S)-methoprene. Each formulation contained 10% w/v fipronil and 10% w/v (S)-methoprene (except in Group 2, in which the formulation contained 10% w/v fipronil and 9% w/v (S)-methoprene) and varied in amount and type of excipients.

Untreated control dogs and dogs in Groups 3 and 4 were infested with 100 adult fleas on Days −1, 7, 14, 21, 28, 35, 42, 49, 56 and 63. Dogs in groups 2 and 5 were infested with fleas on Days −1, 7, 14, 21, 28, 35, 42 and 49. Dogs in Groups 2 and 5 were not infested after D49 because the percent adult flea efficacy fell below 90% for these two groups. For flea infestations, approximately 100 unfed adult C. felis fleas were placed along the lateral midline of each animal from the shoulder to the hip. Dogs were restrained for sufficient time to allow the fleas to penetrate the hair coat.

Fleas were counted and removed by combing approximately 48 hours after treatment or subsequent infestation. Percent efficacy of the formulations as compared to the untreated control group against the adult fleas at each time point was determined.

Flea eggs were collected and incubated in the untreated control dogs and dogs in Groups 2 and 5 on Day 51 and in the untreated control dogs and dogs in Groups 3 and 4 on Day 65. On the day prior to flea egg collection, the cage was prepared for egg collection, and food and water were removed to allow flea eggs to be collected for 24 hours. The eggs were thereafter incubated at 20.7 to 27.5 degrees C. and 69 to 99% relative humidity for 72 hours, and then the hatched larvae were counted. Efficacy of each formulation in preventing flea egg eclosion as compared to the untreated control group was then determined.

Results and Discussion

Flea adulticide activity due to the combination formulations was maintained ≥90% as follows. The number in the parenthesis is the actual adulticide efficacy at the end of time indicated.

Group 2: 44 days (90.7%)
Group 3: 58 days (92.2%)
Group 4: 65 days (91.1%)
Group 5: 37 days (95.0%)

Figure 1:
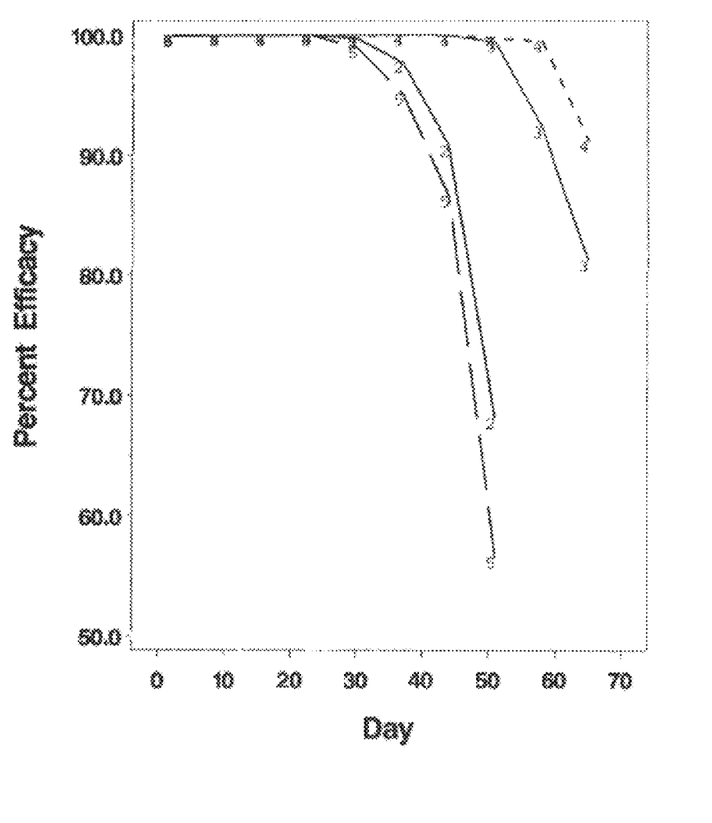
FIG. 1 shows a plot of the percentage efficacy of four different formulations of fipronil and (s)-methoprene (Treatment Groups 2-5) against fleas in dogs. Further details of the experiment are described in the accompanying examples.

A summary of the flea adulticide efficacy over the time of the study is provided in Table 1 below, and FIG. 1.

TABLE 1

Table 1: Flea Adulticide Percent Efficacy

| | Study Day of Flea Count | | | | | | | | | |
|---|---|---|---|---|---|---|---|---|---|---|
| | 2 | 9 | 16 | 23 | 30 | 37 | 44 | 51 | 58 | 65 |
| Group 2 | 100 | 100 | 100 | 100 | 99.7 | 97.7 | 90.7 | 68.0 | NA | NA |
| Group 3 | 100 | 100 | 100 | 100 | 100 | 100 | 100 | 99.4 | 92.2 | 81.1 |
| Group 4 | 100 | 100 | 100 | 100 | 100 | 100 | 100 | 99.7 | 99.4 | 91.1 |
| Group 5 | 99.9 | 100 | 100 | 100 | 99.0 | 95.0 | 86.6 | 56.4 | NA | NA |

These results indicate that all the various formulations of fipronil and (S)-methoprene provided excellent efficacy (≥90%) against adult fleas for at least 35 days, and two formulations were highly effective through at least 58 days.

The percent efficacies (PE) of all four treated groups was greater than or equal to 99.0% through counts on Day 30.

The PE for FRONTLINE® Plus (Treatment Group 2) was 97.7%, 90.7%, and 68.0% on Days 37, 44, and 51, respectively; it received no further infestations.

The PE for Treatment Group 5 was 95.0%, 86.6%, and 56.4% on Days 37, 44, and 51, respectively; it too received no further infestations.

The PE for Treatment Group 3 was 100.0%, 100.0%, 99.4%, 92.2%, and 81.1% on Days 37, 44, 51, 58, and 65, respectively.

The PE for Treatment Group 4 was 100.0%, 100.0%, 99.7%, 99.4%, and 91.1% on Days 37, 44, 51, 58, and 65, respectively.

For all treated groups over all infestation days, the treated and control groups were significantly different at the 5% significance level (p≤0.034; see Table 1).

In particular, it is noted that the spot-on formulations used in Groups 3 and 4 (both of which lack a crystallisation inhibitor) exhibit surprisingly good duration of efficacy compared to Groups 2 (FRONTLINE® Plus) and Group 5 (which contains PVP as a crystallisation inhibitor).

The results of the analysis of the proportion of eggs that hatched into larvae on Days 54 and 68 (following collections on Days 51 and 65, respectively) are presented in Table 2 below.

TABLE 2

Analysis of Proportion of Eggs that Hatch into Larvae

| Study day[2] | Treatment Group[3] | No. of Dogs | Proportion Hatched[4] | Percent Reduction[5] | P-Value[6] |
|---|---|---|---|---|---|
| 54 | 1 | 8 | 0.60 (480/800) | NA[7] | — |
| 54 | 2 | 8 | 0.05 (31/660) | 92.2 | <.001 |
| 54 | 5 | 8 | 0.02 (18/800) | 96.3 | <.001 |
| 68 | 1 | 8 | 0.64 (509/800) | NA | — |
| 68 | 3 | 5 | 0.12 (40/321) | 80.4 | <.001 |
| 68 | 4 | 7 | 0.03 (15/541) | 95.6 | <.001 |

[1]The proportion of eggs that hatched into larvae in the treated groups were compared with the proportion in the Untreated Control group;
[2]Day that egg hatch was counted; eggs were collected on Days 51 and 65, respectively, 48 hours after infestation;
[4]The proportion of eggs that hatched into larvae. The actual number that hatched into larvae over the total number of eggs incubated are listed in the parentheses;
[5]Percent reduction = [(C − T)/C] × 100, where T and C are the proportion of eggs that hatched into larvae for the indicated treated group and the Untreated Control group, respectively;
[6](Two-sided) probability value testing the hypothesis that the population proportion of the indicated treated group was not equal to the population proportion of the Untreated Control group;
[7]Percent reduction with respect to itself.

Eggs were collected from the groups Untreated Control, FRONTLINE® Plus, and Treatment Group 5 on Day 54. Following incubation, the proportion of eggs that hatched in the two treated groups was compared with the Untreated Control group. The percent reduction of eggs that hatched into larvae was 92.2% and 96.3% for FRONTLINE® Plus and Treatment Group 5, respectively. For both, the population means of the treated and Untreated Control groups were significantly different (p<0.001 for both; see Table 2).

Eggs were collected from the groups Untreated Control, Treatment Group 3 and Treatment Group 4 on Day 65. Following incubation, the proportion of eggs that hatched in the two treated groups was compared with the Untreated Control group. The percent reduction of eggs that hatched into larvae was 80.4% and 95.6% for Treatment Groups 3 and Treatment Group 4, respectively.

For both, the population means of the treated and Untreated Control groups were significantly different (p<0.001 for both).

CONCLUSION

In conclusion, all four fipronil: (S)-methoprene formulations provided excellent efficacy against adult flea infestations on dogs and prevented flea egg eclosion for several weeks past the single treatment. All formulations provided flea adulticide activity of ≥90% for at least 35 days and one formulation was highly effective up through 65 days. Moreover, the formulations used in Treatment Group 4 (NMP alone) and Group 3 (DGME alone) were particularly effective.

The results show that fipronil and (S)-methoprene can be formulated in a variety of solvents and excipients and provide excellent activity for several weeks against adult fleas and in the prevention of flea egg eclosion.

The invention is further described with reference to the following numbered paragraphs.

1. A topical formulation comprising:
    (i) fipronil;
    (ii) an IGR;
    (iii) optionally one or more antioxidants; and
    (iv) an organic solvent which is an optionally substituted pyrrolidone;
   wherein said formulation does not contain an organic co-solvent having a boiling point of below 100° C. and a dielectric constant of between 10 and 40.

2. A topical formulation comprising:
    (i) fipronil;
    (ii) an IGR;
    (iii) optionally one or more antioxidants; and
    (iv) an organic solvent which is an optionally substituted pyrrolidone;
   wherein said formulation does not contain ethanol, methanol or isopropanol.

3. A topical formulation according to paragraph 1 or paragraph 2 which does not contain a crystallisation inhibitor.

4. A topical formulation comprising:
(i) fipronil;
(ii) an IGR;
(iii) optionally one or more antioxidants; and
(iv) an organic solvent which is an optionally substituted pyrrolidone;
wherein said formulation does not contain a crystallisation inhibitor.

5. A topical formulation according to paragraph 3 or paragraph 4 wherein the crystallisation inhibitor is selected from:
polyvinylpyrrolidone, a polyvinyl alcohol, a copolymer of vinyl acetate and vinylpyrrolidone, a polyethylene glycol, benzyl alcohol, mannitol, glycerol, sorbitol, a polyoxyethylenated sorbitan ester, lecithin, sodium carboxymethylcellulose and an acrylic derivative;
an anionic surfactant;
a cationic surfactant;
an amine salt of formula N⁺R'R"R'" wherein the radicals R', R" and R'" are each independently an optionally hydroxylated hydrocarbon radical;
a nonionic surfactant; and
an amphoteric surfactant.

6. A topical formulation according to paragraph 4 or paragraph 5 wherein said formulation does not contain an organic co-solvent having a boiling point of below 100° C. and a dielectric constant of between 10 and 40.

7. A topical formulation according to paragraph 4 or paragraph 5 wherein said formulation does not contain ethanol, methanol or isopropanol.

8. A topical formulation according to any preceding paragraph wherein the IGR is selected from cyromazine, lufenuron, 1-(2,6-difluorobenzoyl)-3-(2-fluoro-4-(trifluoromethyl)phenylurea, azadirachtin, diofenolan, fenoxycarb, hydroprene, kinoprene, methoprene, pyriproxyfen, tetrahydroazadirachtin and 4-chloro-2-(2-chloro-2methylpropyl)-5-(6-iodo-3-pyridylmethoxy)pyridizin-3(2H)-one.

9. A topical formulation according to any preceding paragraph wherein the IGR is methoprene.

10. A topical formulation according to any one of paragraphs 1 to 8 wherein the IGR is pyriproxyfen.

11. A topical formulation comprising:
(i) fipronil;
(ii) methoprene;
(iii) optionally one or more antioxidants; and
(iv) an organic solvent which is an optionally substituted pyrrolidone.

12. A topical formulation consisting essentially of:
(i) fipronil;
(ii) methoprene;
(iii) optionally one or more antioxidants; and
(iv) an organic solvent which is an optionally substituted pyrrolidone.

13. A topical formulation consisting of:
(i) fipronil;
(ii) methoprene;
(iii) optionally one or more antioxidants; and
(iv) an organic solvent which is an optionally substituted pyrrolidone.

14. A topical formulation comprising:
(i) fipronil;
(ii) pyriproxyfen;
(iii) optionally one or more antioxidants; and
(iv) an organic solvent which is an optionally substituted pyrrolidone.

15. A topical formulation consisting essentially of:
(i) fipronil;
(ii) pyriproxyfen;
(iii) optionally one or more antioxidants;
(iv) optionally one or more additional active agents; and
(v) an organic solvent which is an optionally substituted pyrrolidone.

16. A topical formulation consisting of:
(i) fipronil;
(ii) pyriproxyfen;
(iii) optionally one or more antioxidants;
(iv) optionally one or more additional active agents; and
(v) an organic solvent which is an optionally substituted pyrrolidone.

17. A topical formulation according to any preceding paragraph wherein the optionally substituted pyrrolidone is selected from 2-pyrrolidone, a 1-($C_{2-20}$-alkyl)-2-pyrrolidone, a 1-($C_{2-10}$-alkenyl)-2-pyrrolidone, a 1-($C_{3-8}$-cycloalkyl)-2-pyrrolidone, a 1-($C_{1-6}$-hydroxyalkyl)-2-pyrrolidone, a 1-($C_{1-6}$-alkoxy-$C_{1-6}$alkyl)-2-pyrrolidone and 1-benzylpyrrolidone.

18. A topical formulation according to any preceding paragraph wherein the optionally substituted pyrrolidone is selected 1-methylpyrrolidone (NMP), 1-ethylpyrrolidone, 1-octylpyrrolidone, 1-dodecylpyrrolidone, 1-isopropylpyrrolidone, 1-(s-butyl)-pyrrolidone, 1-(t-butyl)-pyrrolidone, 1-(n-butyl)-pyrrolidone, 1-hexylpyrrolidone, 1-vinyl-2-pyrrolidone, 1-cyclohexylpyrrolidone, 1-(2-hydroxyethyl)-pyrrolidone, 1-(3-hydroxypropyl)-pyrrolidone, 1-(2-methoxyethyl)-pyrrolidone, 1-(3-methoxypropyl)-pyrrolidone and 1-benzylpyrrolidone, and mixtures thereof.

19. A topical formulation according to any preceding paragraph wherein the optionally substituted pyrrolidone is N-methylpyrrolidone (NMP).

20. A topical formulation according to any preceding paragraph wherein the fipronil is present in an amount of from about 1 to about 20% (w/v).

21. A topical formulation according to paragraph 20 wherein the fipronil is present in an amount of from about 5 to about 15% (w/v), more preferably from about 8 to about 12% (w/v), even more preferably from about 9 to about 11% (w/v).

22. A topical formulation according to any one of paragraphs 1 to 10 wherein the IGR is present in an amount of from about 1 to about 20% (w/v).

23. A topical formulation according to paragraph 22 wherein the IGR is present in an amount of from about 5 to about 15% (w/v), more preferably from about 8 to about 12% (w/v), even more preferably from about 9 to about 11% (w/v).

24. A topical formulation according to any one of paragraphs 11 to 13 wherein the methoprene is present in an amount of from about 1 to about 20% (w/v).

25. A topical formulation according to paragraph 24 wherein the methoprene is present in an amount of from about 5 to about 15% (w/v), more preferably from about 8 to about 12% (w/v), even more preferably from about 9 to about 11% (w/v).

26. A topical formulation according any one of paragraphs 14 to 16 wherein the pyriproxyfen is present in an amount of from about 1 to about 20% (w/v).

27. A topical formulation according to paragraph 26 wherein the pyriproxyfen is present in an amount of from about 5 to about 15% (w/v), more preferably from about 8 to about 12% (w/v), even more preferably from about 9 to about 11% (w/v).

28. A topical formulation consisting essentially of:
about 10% fipronil (w/v);
about 10% (S)-methoprene (w/v); and
QS N-methylpyrrolidone.

29. A topical formulation consisting essentially of:
about 10% fipronil (w/v);
about 10% pyriproxyfen (w/v); and
QS N-methylpyrrolidone.
30. A topical formulation consisting of:
about 10% fipronil (w/v);
about 10% (S)-methoprene (w/v); and
QS N-methylpyrrolidone.
31. A topical formulation consisting of:
about 10% fipronil (w/v);
about 10% pyriproxyfen (w/v); and
QS N-methylpyrrolidone.
32. A topical formulation comprising:
(i) fipronil in an amount of from about 10 to about 20% w/v;
(ii) an IGR in an amount of from about 10 to about 20% w/v;
(iii) optionally one or more antioxidants; and
(iv) an organic solvent which is glycol ether;
wherein said formulation does not contain an organic co-solvent having a boiling point of below 100° C. and a dielectric constant of between 10 and 40.
33. A topical formulation comprising:
(i) fipronil in an amount of from about 10 to about 20% w/v;
(ii) an IGR in an amount of from about 10 to about 20% w/v;
(iii) optionally one or more antioxidants; and
(iv) an organic solvent which is glycol ether;
wherein said formulation does not contain ethanol, methanol or isopropanol.
34. A topical formulation according to paragraph 32 or paragraph 33 which does not contain a crystallisation inhibitor.
35. A topical formulation comprising:
(i) fipronil in an amount of from about 10 to about 20% w/v;
(ii) an IGR in an amount of from about 10 to about 20% w/v;
(iii) optionally one or more antioxidants; and
(iv) an organic solvent which is a glycol ether;
wherein said formulation does not contain a crystallisation inhibitor.
36. A topical formulation according to paragraph 34 or paragraph 35 wherein the crystallisation inhibitor is selected from:
polyvinylpyrrolidone, a polyvinyl alcohol, a copolymer of vinyl acetate and vinylpyrrolidone, a polyethylene glycol, benzyl alcohol, mannitol, glycerol, sorbitol, a polyoxyethylenated sorbitan ester; lecithin, sodium carboxymethylcellulose and an acrylic derivative;
an anionic surfactant;
a cationic surfactant;
an amine salt of formula N⁺R'R''R''' wherein the radicals R', R'' and R''' are each independently an optionally hydroxylated hydrocarbon radical;
a nonionic surfactant; and
an amphoteric surfactant.
37. A topical formulation according to paragraph 35 or paragraph 36 wherein said formulation does not contain an organic co-solvent having a boiling point of below 100° C. and a dielectric constant of between 10 and 40.
38. A topical formulation according to paragraph 35 or paragraph 36 wherein said formulation does not contain ethanol, methanol or isopropanol.
39. A topical formulation comprising:
(i) fipronil;
(ii) an IGR;
(iii) optionally one or more antioxidants; and
(iv) an organic solvent which is a glycol ether selected from methyl diglycol, ethyl diglycol, propyl diglycol, butyl diglycol, methyl glycol, ethyl glycol, dipropylene glycol n-butyl ether, ethylene glycol monoethyl ether, ethylene glycol monomethyl ether, dipropylene glycol monomethyl ether, diethylene glycol monobutyl ether, diethylene glycol monomethyl ether, ethylene glycol monobutyl ether, propylene glycol monomethyl ether, and mixtures thereof;
wherein said formulation does not contain an organic co-solvent having a boiling point of below 100° C. and a dielectric constant of between 10 and 40.
40. A topical formulation comprising:
(i) fipronil;
(ii) an IGR;
(iii) optionally one or more antioxidants; and
(iv) an organic solvent which is a glycol ether selected from methyl diglycol, ethyl diglycol, propyl diglycol, butyl diglycol, methyl glycol, ethyl glycol, dipropylene glycol n-butyl ether, ethylene glycol monoethyl ether, ethylene glycol monomethyl ether, dipropylene glycol monomethyl ether, diethylene glycol monobutyl ether, diethylene glycol monomethyl ether, ethylene glycol monobutyl ether, propylene glycol monomethyl ether, and mixtures thereof;
wherein said formulation does not contain ethanol, methanol or isopropanol.
41. A topical formulation according to paragraph 39 or paragraph 40 which does not contain a crystallisation inhibitor.
42. A topical formulation comprising:
(i) fipronil;
(ii) an IGR;
(iii) optionally one or more antioxidants; and
(iv) an organic solvent which is a glycol ether selected from methyl diglycol, ethyl diglycol, propyl diglycol, butyl diglycol, methyl glycol, ethyl glycol, dipropylene glycol n-butyl ether, ethylene glycol monoethyl ether, ethylene glycol monomethyl ether, dipropylene glycol monomethyl ether, diethylene glycol monobutyl ether, diethylene glycol monomethyl ether, ethylene glycol monobutyl ether, propylene glycol monomethyl ether, and mixtures thereof;
wherein said formulation does not contain a crystallisation inhibitor.
43. A topical formulation according to paragraph 41 or paragraph 42 wherein the crystallisation inhibitor is selected from:
polyvinylpyrrolidone, a polyvinyl alcohol, a copolymer of vinyl acetate and vinylpyrrolidone, a polyethylene glycol, benzyl alcohol, mannitol, glycerol, sorbitol, a polyoxyethylenated sorbitan ester; lecithin, sodium carboxymethylcellulose and an acrylic derivative;
an anionic surfactant;
a cationic surfactant;
an amine salt of formula N⁺R'R''R''' wherein the radicals R', R'' and R''' are each independently an optionally hydroxylated hydrocarbon radical;
a nonionic surfactant; and
an amphoteric surfactant.
44. A topical formulation according to paragraph 42 or paragraph 43 wherein said formulation does not contain an organic co-solvent having a boiling point of below 100° C. and a dielectric constant of between 10 and 40.
45. A topical formulation according to paragraph 42 or paragraph 43 wherein said formulation does not contain ethanol, methanol or isopropanol.
46. A topical formulation according to any one of paragraphs 32 to 45 wherein the IGR is selected from cyromazine, lufenuron, 1-(2,6-difluorobenzoyl)-3-(2-fluoro-4-(trifluoromethyl)phenylurea, azadirachtin, diofenolan, fenoxycarb, hydroprene, kinoprene, methoprene, pyriproxyfen, tetrahydroazadirachtin and 4-chloro-2-(2-chloro-2methylpropyl)-5-(6-iodo-3-pyridylmethoxy)pyridizin-3(2H)-one.

47. A topical formulation according to paragraph 46 wherein the IGR is methoprene.

48. A topical formulation according to paragraph 46 wherein the IGR is pyriproxyfen.

49. A topical formulation comprising:
(i) fipronil;
(ii) pyriproxyfen;
(iii) optionally one or more antioxidants; and
(iv) an organic solvent which is glycol ether;
wherein said formulation does not contain an organic co-solvent having a boiling point of below 100° C. and a dielectric constant of between 10 and 40.

50. A topical formulation comprising:
(i) fipronil;
(ii) pyriproxyfen;
(iii) optionally one or more antioxidants; and
(iv) an organic solvent which is glycol ether;
wherein said formulation does not contain ethanol, methanol or isopropanol.

51. A topical formulation according to paragraph 49 or paragraph 50 which does not contain a crystallisation inhibitor.

52. A topical formulation comprising:
(i) fipronil;
(ii) pyriproxyfen;
(iii) optionally one or more antioxidants; and
(iv) an organic solvent which is a glycol ether;
wherein said formulation does not contain a crystallisation inhibitor.

53. A topical formulation according to paragraph 51 or paragraph 52 wherein the crystallisation inhibitor is selected from:
polyvinylpyrrolidone, a polyvinyl alcohol, a copolymer of vinyl acetate and vinylpyrrolidone, a polyethylene glycol, benzyl alcohol, mannitol, glycerol, sorbitol, a polyoxyethylenated sorbitan ester; lecithin, sodium carboxymethylcellulose and an acrylic derivative;
an anionic surfactant;
a cationic surfactant;
an amine salt of formula N⁺R'R''R''' wherein the radicals R', R'' and R''' are each independently an optionally hydroxylated hydrocarbon radical;
a nonionic surfactant; and
an amphoteric surfactant.

54. A topical formulation according to paragraph 52 or paragraph 53 wherein said formulation does not contain an organic co-solvent having a boiling point of below 100° C. and a dielectric constant of between 10 and 40.

55. A topical formulation according to paragraph 52 or paragraph 53 wherein said formulation does not contain ethanol, methanol or isopropanol.

56. A topical formulation according to any one of paragraphs 39 to 55 wherein the fipronil is present in an amount of from about 1 to about 20% (w/v).

57. A topical formulation according to paragraph 56 wherein the fipronil is present in an amount of from about 5 to about 15% (w/v), more preferably from about 8 to about 12% (w/v), even more preferably from about 9 to about 11% (w/v).

58. A topical formulation according to any one of paragraphs 39 to 57 wherein the IGR is present in an amount of from about 1 to about 20% (w/v).

59. A topical formulation according to paragraph 58 wherein the IGR is present in an amount of from about 5 to about 15% (w/v), more preferably from about 8 to about 12% (w/v), even more preferably from about 9 to about 11% (w/v).

60. A topical formulation according to paragraph 47 wherein the methoprene is present in an amount of from about 1 to about 20% (w/v).

61. A topical formulation according to paragraph 60 wherein the methoprene is present in an amount of from about 5 to about 15% (w/v), more preferably from about 8 to about 12% (w/v).

62. A topical formulation according to paragraph 60 wherein the methoprene is present in an amount of about 9 to about 11% (w/v).

63. A topical formulation according any one of paragraphs 48 to 57 wherein the pyriproxyfen is present in an amount of from about 1 to about 20% (w/v).

64. A topical formulation according to paragraph 63 wherein the pyriproxyfen is present in an amount of from about 5 to about 15% (w/v), more preferably from about 8 to about 12% (w/v), even more preferably from about 9 to about 11% (w/v).

65. A topical formulation consisting essentially of:
(i) fipronil in an amount of about 10 to about 20% w/v;
(ii) methoprene in an amount of about 10 to about 20% w/v; and
(iii) optionally one or more antioxidants; and
(iv) an organic solvent which is a glycol ether.

66. A topical formulation consisting of:
(i) fipronil in an amount of about 10 to about 20% w/v;
(ii) methoprene in an amount of about 10 to about 20% w/v; and
(iii) optionally one or more antioxidants; and
(iv) an organic solvent which is a glycol ether.

67. A topical formulation consisting essentially of:
(i) fipronil;
(ii) pyriproxyfen;
(iii) optionally one or more antioxidants; and
(iii) a veterinarily acceptable carrier which is a glycol ether.

68. A topical formulation consisting of:
(i) fipronil;
(ii) pyriproxyfen;
(iii) optionally one or more antioxidants; and
(iii) a veterinarily acceptable carrier which is a glycol ether.

69. A topical formulation according to any one of paragraph 32 to 38 and 49 to 68 wherein the glycol ether is selected from methyl diglycol, ethyl diglycol, propyl diglycol, butyl diglycol, methyl glycol, ethyl glycol, dipropylene glycol n-butyl ether, ethylene glycol monoethyl ether, ethylene glycol monomethyl ether, dipropylene glycol monomethyl ether, diethylene glycol monoethyl ether (DGME), diethylene glycol monobutyl ether, diethylene glycol monomethyl ether, ethylene glycol monobutyl ether, propylene glycol monomethyl ether, and mixtures thereof.

70. A topical formulation according to paragraph 69 wherein the glycol ether is diethylene glycol monoethyl ether (DGME).

71. A topical formulation consisting essentially of:
about 10% fipronil (w/v);
about 10% (S)-methoprene (w/v); and
QS diethylene glycol monoethylether (DGME).

72. A topical formulation consisting essentially of:
about 10% fipronil (w/v);
about 10% pyriproxyfen (w/v); and
QS diethyleneglycol monoethylether (DGME).

73. A topical formulation consisting of:
about 10% fipronil (w/v);
about 10% (S)-methoprene (w/v); and
QS diethylene glycol monoethylether (DGME).
74. A topical formulation consisting of:
about 10% fipronil (w/v);
about 10% pyriproxyfen (w/v); and
QS diethyleneglycol monoethylether (DGME).
75. A topical formulation according to any one of paragraphs 1 to 27 and 32 to 72 wherein the formulation comprises one or more antioxidants.
76. A topical formulation according to paragraph 75 wherein the total amount of antioxidant present is from about 0.005 to about 1% (w/v), more preferably from about 0.01 to about 0.05% (w/v).
77. A topical formulation according to paragraph 75 or paragraph 76 wherein the antioxidant is selected from butylhydroxyanisole, butylhydroxytoluene, ascorbic acid, sodium metabisulphite, propyl gallate and sodium thiosulphate, and mixtures thereof.
78. A topical formulation according to any preceding paragraph which is a spot-on formulation.
79. A topical formulation according to any preceding paragraph which is prepared for a dose of from 0.1 to 40 mg/kg of fipronil and from 0.1 to 40 mg/kg of the IGR.
80. A topical formulation according to paragraph 79 which is prepared for a dose of from 1 to 20 mg/kg of fipronil and from 1 to 30 mg/kg of the IGR.
81. A topical formulation according to paragraph 79 which is prepared for a dose of from 2 to 10 mg/kg of fipronil and from 2 to 20 mg/kg of the IGR.
82. A topical formulation consisting essentially of:
about 10% fipronil (w/v);
about 5% pyriproxyfen (w/v); and
QS diethylene glycol monoethylether (DGME).
83. A topical formulation consisting of:
about 10% fipronil (w/v);
about 5% pyriproxyfen (w/v); and
QS diethylene glycol monoethylether (DGME).
84. A topical formulation consisting essentially of:
about 5% fipronil (w/v);
about 20% pyriproxyfen (w/v); and
QS diethylene glycol monoethylether (DGME).
85. A topical formulation consisting of:
about 5% fipronil (w/v);
about 20% pyriproxyfen (w/v); and
QS diethylene glycol monoethylether (DGME).
86. A topical formulation consisting essentially of:
about 10% fipronil (w/v);
about 20% (S)-methoprene (w/v); and
QS diethylene glycol monoethylether (DGME).
87. A topical formulation consisting of:
about 10% fipronil (w/v);
about 20% (S)-methoprene (w/v); and
QS diethylene glycol monoethylether (DGME).
88. A topical formulation consisting essentially of:
about 10% fipronil (w/v);
about 10% (S)-methoprene (w/v);
about 5% polyvinyl pyrrolidone (w/v);
about 5% (w/v) polysorbate 80; and
QS diethylene glycol monoethylether (DGME).
89. A topical formulation consisting of:
about 10% fipronil (w/v);
about 10% (S)-methoprene (w/v);
about 5% polyvinyl pyrrolidone (w/v);
about 5% (w/v) polysorbate 80; and
QS diethylene glycol monoethylether (DGME).
90. A topical formulation consisting essentially of:
about 10% fipronil (w/v);
about 10% pyriproxyfen (w/v);
about 5% polyvinyl pyrrolidone (w/v);
about 5% (w/v) polysorbate 80; and
QS diethyleneglycol monoethylether (DGME).
91. A topical formulation consisting of:
about 10% fipronil (w/v);
about 10% pyriproxyfen (w/v);
about 5% polyvinyl pyrrolidone (w/v);
about 5% (w/v) polysorbate 80; and
QS diethyleneglycol monoethylether (DGME).
92. A topical formulation consisting essentially of:
about 10% fipronil (w/v);
about 10% (S)-methoprene (w/v);
about 5% polyvinyl pyrrolidone (w/v);
about 5% (w/v) polysorbate 80; and
QS N-methylpyrrolidone.
93. A topical formulation consisting of:
about 10% fipronil (w/v);
about 10% (S)-methoprene (w/v);
about 5% polyvinyl pyrrolidone (w/v);
about 5% (w/v) polysorbate 80; and
QS N-methylpyrrolidone.
94. A topical formulation consisting essentially of:
about 10% fipronil (w/v);
about 10% pyriproxyfen (w/v);
about 5% polyvinyl pyrrolidone (w/v);
about 5% (w/v) polysorbate 80; and
QS N-methylpyrrolidone.
95. A topical formulation consisting of:
about 10% fipronil (w/v);
about 10% pyriproxyfen (w/v);
about 5% polyvinyl pyrrolidone (w/v);
about 5% (w/v) polysorbate 80; and
QS N-methylpyrrolidone.
96. A topical formulation consisting essentially of:
about 5% fipronil (w/v);
about 5% pyriproxyfen (w/v); and
QS diethylene glycol monoethylether (DGME).
97. A topical formulation consisting of:
about 5% fipronil (w/v);
about 5% pyriproxyfen (w/v); and
QS diethylene glycol monoethylether (DGME).
98. A topical formulation consisting essentially of:
about 10% fipronil (w/v);
about 5% pyriproxyfen (w/v); and
QS diethylene glycol monoethylether (DGME):EtOH 8:1.
99. A topical formulation consisting of:
about 10% fipronil (w/v);
about 5% pyriproxyfen (w/v); and
QS diethylene glycol monoethylether (DGME):EtOH 8:1.
100 A topical formulation consisting essentially of:
about 10% fipronil (w/v);
about 20% (S)-methoprene (w/v);
QS diethylene glycol monoethylether (DGME):EtOH 8:1.
101. A topical formulation consisting of:
about 10% fipronil (w/v);
about 20% (S)-methoprene (w/v);
QS diethylene glycol monoethylether (DGME):EtOH 8:1.
102. A topical formulation consisting essentially of:
about 10% fipronil (w/v);
about 5% pyriproxyfen (w/v);
about 5% polyvinyl pyrrolidone (w/v);
about 5% (w/v) polysorbate 80; and
QS diethyleneglycol monoethylether (DGME):EtOH 8:1

103. A topical formulation consisting of:
about 10% fipronil (w/v);
about 10% pyriproxyfen (w/v);
about 5% polyvinyl pyrrolidone (w/v);
about 5% (w/v) polysorbate 80; and
QS diethyleneglycol monoethylether (DGME):EtOH 8:1
104. A topical formulation consisting essentially of:
about 10% fipronil (w/v);
about 20% (S)-methoprene (w/v);
about 5% polyvinyl pyrrolidone (w/v);
about 5% (w/v) polysorbate 80; and
QS diethyleneglycol monoethylether (DGME):EtOH 8:1
105. A topical formulation consisting of:
about 10% fipronil (w/v);
about 20% (S)-methoprene (w/v);
about 5% polyvinyl pyrrolidone (w/v);
about 5% (w/v) polysorbate 80; and
QS diethyleneglycol monoethylether (DGME):EtOH 8:1
106. A topical formulation consisting essentially of:
about 10% fipronil (w/v);
about 5% pyriproxyfen (w/v);
about 5% polyvinyl pyrrolidone (w/v);
about 5% (w/v) polysorbate 80;
about 0.025% (w/v) BHA; and
QS diethyleneglycol monoethylether (DGME):EtOH 8:1.
107. A topical formulation consisting of:
about 10% fipronil (w/v);
about 5% pyriproxyfen (w/v);
about 5% polyvinyl pyrrolidone (w/v);
about 5% (w/v) polysorbate 80;
about 0.025% (w/v) BHA; and
QS diethyleneglycol monoethylether (DGME):EtOH 8:1.
108. A topical formulation consisting essentially of:
about 10% fipronil (w/v);
about 20% (S)-methoprene (w/v);
about 5% polyvinyl pyrrolidone (w/v);
about 5% (w/v) polysorbate 80;
about 0.025% (w/v) BHA; and
QS diethyleneglycol monoethylether (DGME):EtOH 8:1.
109. A topical formulation consisting of:
about 10% fipronil (w/v);
about 20% (S)-methoprene (w/v);
about 5% polyvinyl pyrrolidone (w/v);
about 5% (w/v) polysorbate 80;
about 0.025% (w/v) BHA; and
QS diethyleneglycol monoethylether (DGME):EtOH 8:1.
110. A topical formulation according to any preceding paragraph for use in treating or controlling an ectoparasite infestation on an animal.
111. A topical formulation for use according to paragraph 110 wherein the animal is a domestic animal.
112. A topical formulation for use according to paragraph 110 wherein the animal is a dog or a cat.
113. A topical formulation for use according to paragraph 110 wherein the ectoparasite is a flea.
114. A topical formulation for use according to paragraph 110 wherein the ectoparasite is a tick.
115. A method of treating or controlling an ectoparasite on an animal, said method comprising topically applying a topical composition according to any one of paragraphs 1 to 109 to said animal.
116. A method according to paragraph 115 wherein the animal is a domestic animal.
117. A method according to paragraph 115 wherein the animal is a dog or a cat.
118. A method according to paragraph 115 wherein the ectoparasite is a flea.
119. A method according to paragraph 115 wherein the ectoparasite is a tick.
120. A method according to paragraph 115 wherein the topical composition is applied to a localised area having a surface area of 10 cm$^3$ or less.
121. A method according to paragraph 115 wherein the topical composition is applied to a localised area between the animal's shoulder blades.
122. A method according to paragraph 115 wherein the topical composition is applied at one or two points.
123. A topical formulation, use or method substantially as described herein.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

What is claimed is:
1. A topical formulation consisting of:
(i) 5 to 15% (w/v) fipronil;
(ii) 5 to 15% (w/v) methoprene;
(iii) one or more antioxidants; and
(iv) an organic solvent which is N-methylpyrrolidone.
2. The topical formulation of claim 1, wherein fipronil is present in a concentration of 8 to 12% (w/v).
3. The topical formulation of claim 1, wherein methoprene is present in a concentration of 8 to 12% (w/v).
4. The topical formulation of claim 1, wherein the antioxidant is selected from the group consisting of butylhydroxyanisole, butylhydroxytoluene, ascorbic acid, sodium metabisulphite, propyl gallate and sodium thiosulphate, and mixtures thereof.
5. The topical formulation of claim 4, wherein the antioxidant is butylhydroxyanisole or butylhydroxytoluene, or a combination thereof.

* * * * *